United States Patent [19]

Inaba et al.

[11] Patent Number: 4,923,871
[45] Date of Patent: May 8, 1990

[54] CERTAIN 2,6-DIMETHYL-4-(PYRAZOLO[1,5A]-PYRIDIN-3-YL)1,4-DIHYDRO-PYRIDINE-3,5-DICARBOXYLATE DERIVATIVES AND COMPOSITIONS CONTAINING SAME

[75] Inventors: Makoto Inaba, Tokyo; Hirotaka Shinoda; Fujio Iinuma, both of Saitama, all of Japan

[73] Assignees: Kyorin Seiyaku Kabushiki Kaisha; Japanese Foundation for Cancer Research, both of Tokyo, Japan

[21] Appl. No.: 125,373

[22] Filed: Nov. 25, 1987

[30] Foreign Application Priority Data

Nov. 26, 1986 [JP] Japan ................................ 61-281093

[51] Int. Cl.$^5$ ................. C07D 401/04; C07D 241/04; A61K 31/44; A61K 31/495
[52] U.S. Cl. ................................ 514/255; 544/362; 546/271; 514/338
[58] Field of Search ................. 546/271; 514/338, 255; 544/362

[56] References Cited

U.S. PATENT DOCUMENTS 4,794,187  12/1988  Glossman ............................ 546/321
4,808,603  2/1989   Eichenberger et al. ............. 514/356
4,808,622  2/1989   Kinast et al. ........................ 514/356

Primary Examiner—Alan L. Rotman
Attorney, Agent, or Firm—McAulay Fisher Nissen & Goldberg

[57] ABSTRACT

This invention relates to new and useful 2,6-dimethyl-4-(pyrazolo[1,5-a]pyridin-3-yl)-1,4-dihydropyridine-3,5-dicarboxylate derivatives of the following formula:

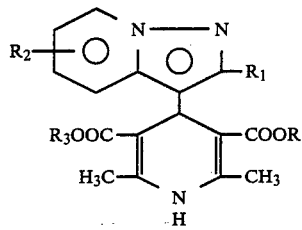

and pharmaceutically acceptable salts thereof, having potent promoting activity of some antitumor agents against various kinds of tumor cells including multiple drug resistant tumor cells.

3 Claims, No Drawings

CERTAIN 2,6-DIMETHYL-4-(PYRAZOLO[1,5A]-PYRIDIN-3-YL)1,4-DIHYDRO-PYRIDINE-3,5-DICARBOXYLATE DERIVATIVES AND COMPOSITIONS CONTAINING SAME

This invention relates to new and useful 2,6-dimethyl-4-(pyrazolo[1,5-a]pyridin-3-yl)-1,4-dihydropyridine-3,5-dicarboxylate derivatives of the following formula:

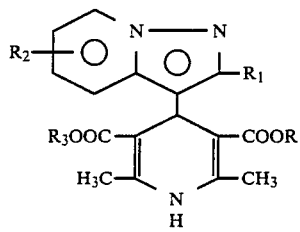

and pharmaceutically acceptable salts thereof, having the potent promoting activity of some antitumor agents against various kinds of tumor cells including multiple drug resistant tumor cells.

BACKGROUND OF THE INVENTION

1. Field of the Invention

This invention relates to new and useful 1,4-dihydropyridine derivatives having the promoting activity of some antitumor agents against various kinds of tumor cells including multiple drug resistant cells and also to their use, and further, to process for the preparation of the novel derivatives.

2. Description of the Prior Art

Research is ongoing to stamp out cancerous growth by using various novel antitumor agents. However, the appearance of resistance to antitumor drugs is a serious problem in the clinical treatment of various tumors and therefore, the circumvention of such resistance is an important subject in the cancer chemotherapy.

Further, there are some intricate factors which make this problem more difficult to solve. In other words, tumor cells resistant to one of the antitumor agents show crossresistance to other antitumor agents (Multiple Drug Resistance: MDR), and overcoming this type of resistance is more difficult in clinical cancer chemotherapy.

Tsuruo et al (CANCER RES., 44, 4303, 1984; 43, 2267, 1983) reported that the drugs used clinically as a calcium channel-blocker, calmodulin inhibitor and antiarrhythmic agent promoted the activity of antitumor gents against resistant tumor cells. Practically, it was found that verapamil, caroverine, clomipramine, trifluoperazine, prenylamine, No. 233 and quinidine enhanced the activity of antitumor agents in vitro against the resistant sub-lines of mouse leukemia cells (P388/VCR, P388/ADR) and also verapamil enhanced the antitumor activity in vivo.

Tsuruo et al (CANCEL RES., 43, 2905, 1983) also reported that diltiazem and nicardipine as a calcium influx antagonist and quinidine as an antiarrhythmic agent promoted the activity of antitumor agents against mouse P388 cells resistant to VCR or ADR (P388/VCR, P388/ADR) in vitro and in vivo.

Promoting agents of antitumor activity reported so far mainly belong to the class of calcium antagonists or blockers. Intracellular calcium ion is the chemical mediator which carries on the physiological function in some particular tissues, that is, plays an important role in the excitation-contraction coupling of heart muscle and also, in the excitation-contraction coupling of vascular smooth muscle. Intracellular distribution and transport of calcium ion play a key role in their physiological function. The pharmacological action of various calcium antagonists is induced as a consequence of inhibition of calcium influx or function.

However, with respect to therapeutic efficacy of the calcium blockers as a promotor of antitumor agents, the striking action of these calcium blockers becomes a factor restricting their usefulness due to serious side-effects and therefore, limits their clinical application.

SUMMARY OF THE INVENTION

We have discovered compounds which overcome these problems. More particularly, the present invention comprises new 2,6-dimethyl-4-(pyrazolo[1,5-a]pyridin-3-yl)-1,4-dihydropyridine-3,5-dicarboxylate derivatives of the formula (I),

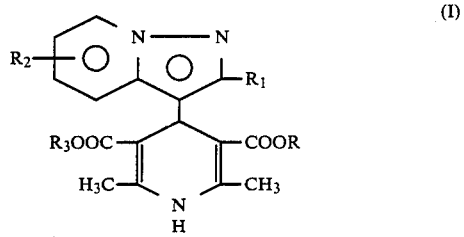

its hydrates and salts, wherein $R_1$ is lower alkyl group, $R_2$ is a hydrogen atom, halogen atom, lower alkoxy, or nitro group, and R and $R_3$ are each independently alkyl, lower alkoxyalkyl, an aralkyl group, or

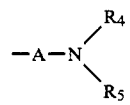

Wherein a is a straight or branched alkylene group, and $R_4$ and $R_5$ are each independently a hydrogen atom, lower alkyl, aralkyl group, or connected with each other to make five- or six-membered heterocycles which may contain other hetero atoms, and a process for their preparations and usage thereof for the cancer chemotherapy.

DETAILED DESCRIPTION OF THE INVENTION

The term "alkyl group" as it is employed herein includes a straight or branched chain containing 1 to 10 carbon atoms, e.g., methyl, isopropyl, octyl group and the like. Lower alkyl group includes a straight or branched chain containing between 1 and 6 carbon atoms, e.g., methyl, ethyl, isopropyl group and the like. Aralkyl group includes a lower alkyl group which is substituted by aryl group, e.g., benzyl, phenethyl and the like. Lower alkoxyalkyl group includes an alkyl group which is substituted by a straight or branched chain containing 1 to 6 carbon atoms, e.g., methoxymethyl, methoxyethyl group and the like. A straight or branched alkylene group includes, e.g., ethylene, 2-methylpropylene group and the like. A five- or six-membered heterocycle which may contain other hetero atom includes, e.g., piperazine, pyrrolidine, piperidine, morpholine, thiomorpholine and the like. Halogen atom includes, e.g., fluorine, chlorine and bromine.

This invention as a result of analyzing these various factors described above, provides novel compounds with the following characteristic properties, (a) They showed low toxicity, negligible Ca-antagonizing and hypotensive activities, and therefore, it may be easy to bring in a clinical application different from that of a calcium blocker.

(b) They were able to completely reverse very high resistance to anthracyclines or vinca-alkaloids in vitro at as low concentration as 0.5–3.0 μg/ml.

(c) This combined treatment with both the antitumor agents and these derivatives clearly induces synergistic antitumor effect in therapeutic experiments.

(d) This combination of relatively low doses of antitumor agents and the compound of this invention in as high a dose as possible is an optimal treatment regimen. Therefore, it may be useful for preventing the serious side-effects of antitumor agents in clinical chemotherapy, because of reducing the dose of the antitumor agents.

(e) This combination treatment exhibits not only clear synergistic effects, but also curable effects with long survival against non-resistant tumor cells, indicating that these novel derivatives are able to overcome the heterogeneity as to sensitivity to antitumor agents in such a cell population.

In conclusion, this type of combination treatment may have therapeutic efficacy not only at the late stage when tumor acquired resistance, is present but also at the initial stage of chemotherapy.

The following explains the preparation process for the compounds of the invention.

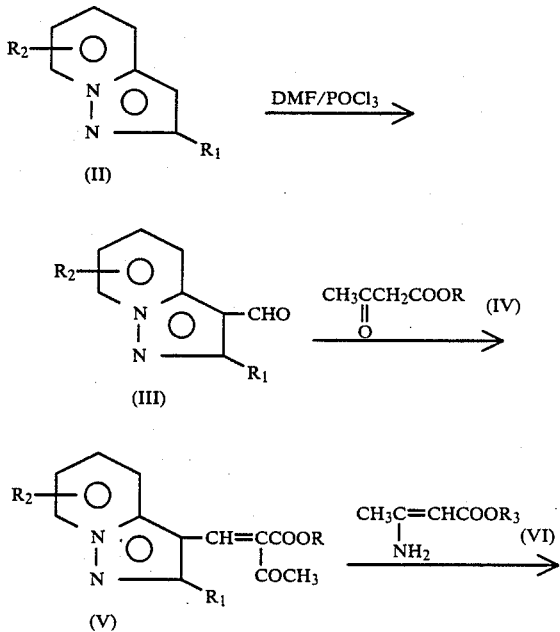

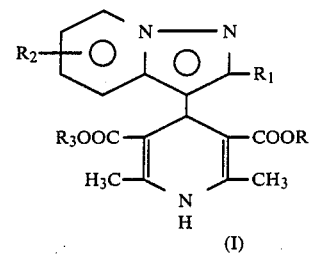

(I)

wherein $R_1$ is lower alkyl group, $R_2$ is a hydrogen atom, halogen atom, lower alkyl, lower alkoxy, or nitro group, and R and $R_3$ are each independently alkyl, lower alkoxyalkyl, aralkyl group, or

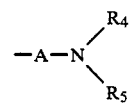

(A is straight or branched alkylene group, and $R_4$ and $R_5$ are each independently a hydrogen atom, lower alkyl, aralkyl group, or connected with each other to make five- or six-membered heterocycles which may contain other hetero atom).

(1) Namely, the starting compounds represented by the formula (II) are formylated in the presence of formylation agents such as phosphorus oxychloride-dimethylformamide (DMF), and so on, to give the compounds represented by the formula (III).

(2) The compounds represented by the formula (III) are condensed with the compounds represented by the formula (IV) in the presence of condensing agents to give the compounds represented by the formula (V). Suitable condensing agents for this reaction are organic and inorganic acids as a acid catalyst, for example, hydrochloric acid, acetic acid and so on, and amines as a base catalyst, for example, piperidine, triethylamine and so on. Benzene, toluene, chloroform, dimethylformamide, tetrahydrofuran, alcohol, or the like may be used as a solvent. The reaction temperature is selected appropriately in a range of 50°–150° C. and the reaction time is selected appropriately in a range of 0.5–15 hours. In more detail, it is preferable to allow compounds represented by the formula (III) to react with 0.8 to 1.5 mole of compounds represented by the formula (IV).

(3) The compounds represented by the formula (V) are condensed with the compounds represented by the formula (VI) to give the compounds represented by the formula (I) in the presence or absence of the solvent by heating. The suitable solvent of this reaction is benzene, toluene, chloroform, dimethylformamide, tetrahydrofuran, alcohols such as isopropylalcohol, or the like. In more detail, it is preferable to allow compounds represented by the formula (V) to react with 0.8 to 1.2 mole of compounds represented by the formula (VI) for 3 to 20 hours at 50°–150° C.

Furthermore, the compounds of the formula (I) can be converted, if desired, to pharmaceutically acceptable acid salts by treatment with acid wherein either of R and $R_3$ are the

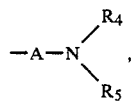

group. The acid may be organic and inorganic acids such as, for example, hydrochloric acid, sulfuric acid, phosphoric acid, acetic acid, methanesulfonic acid, oxalic acid, fumaric acid and lactic acid.

The compound of the formula (I), hydrates and salts thereof may be used as medicine in the conventional form of pharmaceutical preparations, which may be, for example, tablets, capsules, powder, ointment, suppositories, syrup, liquor, suspension, spray or injection, suitable for peroral, parenteral, enteral or local administration.

The following examples will further illustrate the present invention without, however, limiting it thereto.

EXAMPLE 1

Dimethyl 2,6-dimethyl-4-(2-isopropylpyrazolo[1,5-a]pyridin-3-yl)-1,4-dihydropyridine-3,5-dicarboxylate (a) Methyl 2-acetyl-3-(2-isopropylpyrazolo[1,5-a]pyridin-3-yl) acrylate To a solution of 4 g of 3-formyl-2-isopropylpyrazolo[1,5-a]pyridine, 2.7 g of methyl acetoacetate and 256 mg of glacial acetic acid in 11 ml of benzene was added dropwise a solution of 0.36 g of piperidine in 2.2 ml of benzene by a fifth at 20 minutes intervals under stirring at room temperature. After the addition was completed, the mixture was refluxed for 4 hours while resulting azeotropic water was separated by isobaric distillation. Then 40 ml of benzene was added, and washed with 20 ml of saturated sodium hydrogencarbonate, 20 ml of water, and 20 ml of salt water. The benzene solution was dried over anhydrous barium sulfate, and then concentrated to give the title compound in a yield of 5.9 g as a crude dark reddish liquid. Silica gel thin layer chromatography of the title compound gave Rf=0.36 value using benzene as an eluent.

NMR ($\delta$ in CDCl$_3$), 7.66 (1H, s), 6.45–8.33 (4H, m), 3.89 (3H,s), 3.34 (1H, m), 2.46 (3H, s), 1.34 (6H, d, J=6.59 Hz).

(b) A mixture of 5.9 g of methyl 2-acetyl-3-(2-isopropylpyrazolo[1,5-a]pyridin-3-yl)acrylate and 2.5 g of methyl 3-aminocrotonate was stirred for 4.5 hours at 60°–65° C., and then for 8.7 hours at 100°–105° C. The reaction mixture was purified with silica gel column chromatography using benzene-ethyl acetate mixtures as an eluent. The eluate was concentrated and recrystallized from hexane-benzene mixtures to give the title compound in a yield of 2.6 g (31%) as yellow needles, mp 244°–246° C.

Analysis (%) for $C_{21}H_{25}N_3O_4$, Calcd. (Found): C, 65.78 (65.91); H, 6.57 (6.59); 10.96 (10.83).

Using the procedure described in Example 1, following new compounds have been obtained.

EXAMPLE 2

Methyl ethyl 2,6-dimethyl-4-(2-isopropylpyrazolo[1,5-a]pyridin-3-yl)-1,4-dihydropyridine-3,5-dicarboxylate Yield 22%, mp 219°–221.5° C.
Analysis (%) for $C_{22}H_{27}N_3O_4$, Calcd. (Found): C, 66.48 (66.73); H, 6.85 (6.87); 10.57 (10.58).

EXAMPLE 3

Butyl methyl 2,6-dimethyl-4-(2-isopropylpyrazolo[1,5-a]pyridin-3-yl)-1,4-dihydropyridine-3,5-dicarboxylate Yield 21%, mp 160°–161° C.
Analysis (%) for $C_{24}H_{31}N_3O_4$, Calcd. (Found): C, 67.74 (66.79); H, 7.34 (7.46); 9.87 (9.91).

EXAMPLE 4 tert-Butyl methyl 2,6-dimethyl-4-(2-isopropylpyrazolo[1,5-a]pyridin-3-yl)-1,4-dihydropyridine-3,5-dicarboxylate Yield 8%, mp 205.5°–206° C.
Analysis (%) for $C_{24}H_{31}N_3O_4$, Calcd. (Found): C, 67.74 (66.75); H, 7.34 (7.41); 9.87 (9.91).

EXAMPLE 5

Methyl octyl, 2,6-dimethyl-4-(2-isopropylpyrazolo[1,5-a]pyridin-3-yl)-1,4-dihydropyridine-3,5-dicarboxylate Yield 20%, mp 154°–156° C.
Analysis (%) for $C_{28}H_{39}N_3O_4$, Calcd. (Found): C, 69.83 (69.81); H, 8.16 (8.24); 8.72 (8.79).

EXAMPLE 6

N-Benzyl-N-methyl-2-aminoethyl methyl 2,6-dimethyl-4-(2-isopropylpyrazolo[1,5-a]pyridin-3-yl)-1,4-dihydropyridine-3,5-dicarboxylate Yield 14%, mp 172°–175° C.
Analysis (%) for $C_{30}H_{36}N_4O_4 \cdot 0.1\ C_6H_6$, Calcd. (Found): C, 70.08 (69.90); H, 7.03 (7.07); 10.68 (10.47).

EXAMPLE 7

Methyl 2-dimethylaminoethyl 2,6-dimethyl-4-(2-isopropylpyrazolo[1,5-a]pyridin-3-yl)-1,4-dihydropyridine-3,5-dicarboxylate Yield 6%, mp 136°–138° C.
Analysis (%) for $C_{24}H_{32}N_4O_4$, Calcd. (Found): C, 65.43 (65.44); H, 7.32 (7.48); 12.72 (12.98).

EXAMPLE 8

Methyl 2-(4-methyl-1-piperazinyl)ethyl 2,6-dimethyl-4-(2-isopropylpyrazolo[1,5-a]pyridin-3-yl)-1,4-dihydropyridne-3,5-dicarboxylate Yield 6%, mp 102°–104° C.
Analysis (%) for $C_{27}H_{37}N_5O_4 \cdot 0.3\ C_6H_6$, Calcd. (Found): C, 66.64 (66.78); H, 7.53 (7.54); 13.49 (13.25).

EXAMPLE 9

Methyl 2-(N-benzyl-N-methylamino)ethyl 2,6-dimethyl-4-(2-methylpyrazolo[1,5-a]pyridin-3-yl)-1,4-dihydropyridine-3,5-dicarboxylate (a) 3-Formyl-2-methylpyrazolo[1,5-a]pyridine To 116.6 ml of dimethylformamide was added 105 ml of phosphorus oxychloride, followed by 99 g of 2- methylpyrazolo[1,5-a]pyridine under stirring at keeping the temperature below 20° C. The reaction mixture was stirred at 50°–60° C. for 1 hours, then poured into ice water. Acidic aqueous solution was neutralized with potassium carbonate, then extracted with dichloromethane, washed with salt water, dried over anhydrous sodium sulfate and then concentrated. The resulting residue was recrystallized from methanol to give the title compound in a yield of 54.8 g (46%) as colorless crystals, mp 77°–79° C.

(b) Methyl 2-acetyl-3-(2-methylpyrazolo[1,5-a]pyridine-3-yl)acrylate

A solution of 54 g of 3-formyl-2-methylpyrazolo[1,5-a]pyridine, 47.1 g of methyl acetoacetate, 20.6 g of benzoic acid and 2.9 g of piperidine in 200 ml of toluene was refluxed for 9 hours while resulting azeotropic water was separated by isobaric distillation, by adding 2.9 g of piperidine at 3 hour intervals. The reaction mixture was washed with saturated sodium hydrogenecarbonate, then salt water, dried over anhydrous sodium sulfate and then concentrated. After cooling, resulting crystals were removed by filtration to give the title compound in a yield of 40.7 g as a crude dark reddish liquid.

(c)

A solution of 24.9 g of methyl 2-acetyl-3-(2-methyl-pyrazolo[1,5-a]pyridin-3-yl)acrylate and 28.8 g of 2-(N-benzyl-N-methylamino)ethyl 3-aminocrotonate in 125 ml of isopropylalcohol was refluxed for 8.5 hours, then concentrated. The resulting residue was dissolved in 100 ml of ethyl acetate, washed with 1 N-hydrochloric acid, and then extracted with 2 N-hydrochloric acid three times. The resulting hydrochloric acid layer was alkalized with 5 N-aqueous sodium hydroxide at pH 9, and then extracted with ethyl acetate. The ethyl acetate layer was washed with salt water, dried over anhydrous sodium sulfate and then concentrated. Hexane was added to the resulting residue, and insoluble layer was collected, then recrystallized from diethyl ether-hexane mixtures.

The crystals were separated from the solution by filtration, washed with diethyl ether, and then recrystallized from benzenehexane mixed solvent to give the title compound in a yield of 1.6 g (3%) as yellow ocher crystals, mp 118°–120° C.

Analysis (%) for $C_{28}H_{32}N_4O_4$, Calcd. (Found): C, 68.83 (68.85); H, 6.60 (6.72); N, 11.47 (11.35).

THE UTILITY OF THIS INVENTION

EXPERIMENT 1

It was observed that the derivatives of this invention promoted the activity of antitumor agents, and the potency was equal to those of verapamil and nifedipine in vitro culture of P388/VCR and P388/ADR cells. The derivatives showed low values ($pA_{10}$: 5.6–6.1) of calcium antagonizing activity as compared with values of verapamil ($pA_{10}$: 7.5) and nifedipine ($pA_{10}$: 8.8) by assessing the dose-dependent relaxing effect using the Magnus's method with isolated preparation of guinea-pig caecum strip.

From the results of examination on the blood pressure of SHR rats, verapamil and nifedipine as positive control demonstrated the typical effects of calcium antagonist, that is, observed the depression of 41 and 25 mmHg, respectively. However, the derivatives of this invention did not show hypotensive activity in the same experiment (Table 1).

TABLE 1

|  | Promoting Activity to VCR[1] (Minumum effective dose: μg/ml) | Promoting Activity to ADR[2] (Minumum effective dose: μg/ml) | Calcium Antagonizing Activity (pA10)[3] | Hypotensive Activity[4] mg/kg | mmHg |
| --- | --- | --- | --- | --- | --- |
| Example 1 | 3 | — | 5.6 | 30 | ± |
| Example 2 | 3 | — | 5.8 | 30 | ± |
| Example 3 | 1 | 3 | 6.1 | 30 | ± |
| Example 4 | 3 | 3 | 5.6 | 30 | ± |
| Example 5 | 3 | 3 | 5.6 | 30 | ± |
| Example 6 | 1 | 3 | 6.1 | 10 | ± |
| Example 9 | 1 | 3 | 6.0 | 30 | ± |
| Verapamil | 3 | 3 | 7.5 | 10 | 25 |
| Nifedipine | 3 | >3 | 8.8 | 10 | 41 |

[1]Vincristine-resistant subline (P388/VCR) were cultured with $10^{-5}$ mM VCR.
[2]Adriamycin-resistant subline (P388/ADR) were cultured with $3 \times 10^{-4}$ mM ADR.
[3]by Magnus's Method with isolated preparation of guinea-pig caecum strip.
[4]Hypotensive activity (values showed depression of blood pressure) in the SHR rat.

EXPERIMENT 2

One million P388/VCR cells were inoculated intraperitoneally into female $CDF_1$ mice. VCR (0.1 mg/kg) or Example 6 or verapamil (at doses indicated in Table 2) dissolved in sterile physiological saline were administered twice a day (in the morning and evening) intraperitoneally for 5 consecutive days.

Compound of this invention demonstrated significantly better life-prolongation effect in the combined treatment with VCR than that of verapamil. The resistance to VCR of these resistant tumor cells was almost entirely reversed by the compound of this invention (Table 2).

TABLE 2

Therapeutic effect of Example 6 and Verapamil on the P388/VCR (vincristine-resistant subline)-bearing mice.

| VCR mg/kg/day | Dosage mg/kg/day | Period (days) | Survival days | Mean ± S.D. | T/C (%) |
| --- | --- | --- | --- | --- | --- |
| — | Control | — | 5 | 9  9  9  9  9  10 | 9.2 ± 0.4 | (100) |
| 0.1 | — |  | | 11  11  11  12  12  12 | 11.5 ± 0.5 | 125 |
| 0.1 |  | 25 × 2 | | 12  13  13  13  14  15 | 13.3 ± 1.0 | 145 |
| 0.1 | Example 6 | 50 × 2 | 5 | 13  14  15  16  17  18 | 15.5 ± 1.9 | 168 |

TABLE 2-continued

Therapeutic effect of Example 6 and Verapamil on the P388/VCR (vincristine-resistant subline)-bearing mice.

| VCR mg/kg/day | | Dosage mg/kg/day | Period (days) | Survival days | | | | | | Mean ± S.D. | T/C (%) |
|---|---|---|---|---|---|---|---|---|---|---|---|
| 0.1 | | 75 × 2 | | 17 | 18 | 18 | 18 | 18 | 19 | 18.0 ± 0.6 | 196 |
| — | | 25 × 2 | | 9 | 9 | 9 | 10 | 10 | 10 | 9.5 ± 0.5 | 103 |
| — | Example 6 | 50 × 2 | 5 | 9 | 9 | 9 | 9 | 9 | 9 | 9.0 | 98 |
| — | | 75 × 2 | | 9 | 9 | 10 | 10 | 10 | 10 | 9.7 ± 0.5 | 105 |
| — | Control | — | 5 | 9 | 9 | 9 | 9 | 10 | 10 | 9.3 ± 0.5 | (100) |
| 0.1 | | — | | 9 | 9 | 11 | 11 | 12 | 12 | 10.7 ± 1.4 | 115 |
| 0.1 | Verapamil | 25 × 2 | 5 | 13 | 13 | 13 | 13 | 14 | 14 | 13.3 ± 0.5 | 143 |
| 0.1 | | 40 × 2 | | 14 | 15 | 15 | 15 | 15 | 16 | 15.0 ± 0.6 | 161 |
| — | Verapamil | 25 × 2 | 5 | 10 | 10 | 10 | 10 | 10 | 10 | 10.0 | 108 |
| — | | 40 × 2 | | 9 | 10 | 10 | 10 | 10 | 10 | 9.8 ± 0.4 | 105 |

EXPERIMENT 3

The therapeutic effect of the compound of this invention was examined against P388 parent line (sensitive to VCR) in the same condition described in Experiment 2. A dose of VCR (0.1 mg/kg) alone produced about twice life-prolongation effect as compared with the control group, but no cured mouse was observed.

On the other hand, combination treatment with VCR and the compound of this invention resulted in not only the highest life-prolongation effect but also cured mice (one-sixth mouse at dose of 50×2 mg/kg and three-sixth mice at dose of 75×2 mg/kg, respectively).

TABLE 3

Therapeutic effect of Example 6 on the Parent P388 Leukemia (sensitive to VCR)-bearing mice.

| VCR mg/kg/day | Dosage mg/kg/day | | Period (days) | Survival days | | | | | | Mean ± S.D. | No. of cured mice |
|---|---|---|---|---|---|---|---|---|---|---|---|
| — | Control | — | 5 | 9 | 9 | 9 | 9 | 10 | 10 | 9.3 ± 0.5 | 0/6 |
| 0.1 | | | | 16 | 18 | 19 | 19 | 19 | 19 | 18.3 ± 1.2 | 0/6 |
| 0.1 | | 10 × 2 | | 18 | 18 | 18 | 18 | 18 | 19 | 18.2 ± 0.4 | 0/6 |
| 0.1 | Example 6 | 25 × 2 | 5 | 19 | 20 | 20 | 21 | 22 | 22 | 20.7 ± 1.2 | 0/6 |
| 0.1 | | 50 × 2 | | 20 | 22 | 22 | 27 | 28 | | 23.8 ± 3.5 | 1/6 |
| 0.1 | | 75 × 2 | | 29 | 31 | 32 | | | | 30.7 ± 1.5 | 3/6 |
| — | Example 6 | 75 × 2 | 5 | 10 | 10 | 10 | 11 | 11 | 11 | 10.5 ± 1.5 | 0/6 |

What is claimed is:

1. A compound selected from the group consisting of
dimethyl 2,6-dimethyl-4-(2-isopropylpyrazolo[1,5-a]pyridin-3-yl)-1,4-dihydropyridine-3,5-dicarboxylate;
methyl ethyl 2,6-dimethyl-4-(2-isopropylpyrazolo-[1,5-a]pyridin-3-yl)-1,4-dihydropyridine-3,5-dicarboxylate;
butyl methyl 2,6-dimethyl-4-(2-isopropylpyrazolo-[1,5-a]pyridin-3-yl)-1,4-dihydropyridine-3,5-dicarboxylate;
tert-butyl methyl 2,6-dimethyl-4-(2-isopropylpyrazolo-[1,5-a]pyridin-3-yl)-1,4-dihydropyridine-3,5-dicarboxylate;
methyl octyl 2,6-dimethyl-4-(2-isopropylpyrazolo-[1,5-a]pyridin-3-yl)-1,4-dihydropyridine-3,5-dicarboxylate;
N-benzyl-N-methyl-2-aminoethyl methyl 2,6-dimethyl-4-(2-isopropylpyrazolo-[1,5-a]pyridin-3-yl)-1,4-dihydropyridine-3,5-dicarboxylate;
methyl 2-dimethylaminoethyl 2,6-dimethyl-4-(2-isopropylpyrazolo-[1,5-a]pyridin-3-yl)-1,4-dihydropyridine-3,5-dicarboxylate;
methyl 2-(4-methyl-1-piperazinyl)ethyl 2,6-dimethyl-4-(2-isopropylpyrazolo-[1,5-a]pyridin-3-yl)-1,4-dihydropyridine-3,5-dicarboxylate; and
methyl 2-(N-benzyl-N-methylamino)ethyl 2,6-dimethyl-4-(2-isopropylpyrazolo-[1,5-a]pyridin-3-yl)-1,4-dihydropyridine-3,5-dicarboxylate.

2. A pharmaceutical composition comprising an antitumor activity promoting effective amount of the compound of claim 1 and a pharmaceutically acceptable carrier.

3. The composition of claim 1 wherein the compound is selected from the group consisting of
dimethyl 2,6-dimethyl-4-(2-isopropylpyrazolo[1,5-a]pyridin-3-yl)-1,4-dihydropyridine-3,5-dicarboxylate;
methyl ethyl 2,6-dimethyl-4-(2-isopropylpyrazolo-[1,5-a]pyridin-3-yl)-1,4-dihydropyridine-3,5-dicarboxylate;
butyl methyl 2,6-dimethyl-4-(2-isopropylpyrazolo-[1,5-a]pyridin-3-yl)-1,4-dihydropyridine-3,5-dicarboxylate;
tert-butyl methyl 2,6-dimethyl-4-(2-isopropylpyrazolo-[1,5-a]pyridin-3-yl)-1,4-dihydropyridine-3,5-dicarboxylate;
methyl octyl 2,6-dimethyl-4-(2-isopropylpyrazolo-[1,5-a]pyridin-3-yl)-1,4-dihydropyridine-3,5-dicarboxylate;
N-benzyl-N-methyl-2-aminoethyl methyl 2,6-dimethyl-4-(2-isopropylpyrazolo-[1,5-a]pyridin-3-yl)-1,4-dihydropyridine-3,5-dicarboxylate;
methyl 2-dimethylaminoethyl 2,6-dimethyl-4-(2-isopropylpyrazolo-[1,5-a]pyridin-3yl)-1,4-dihydropyridine-3,5-dicarboxylate;
methyl 2-(4-methyl-1-piperazinyl)ethyl 2,6-dimethyl-4-(2-isopropylpyrazolo-[1,5-a]pyridin-3-yl)-1,4-dihydropyridine-3,5-dicarboxylate; methyl 2-(N-benzyl-N-methylamino)ethyl 2,6-dimethyl-4-(2-isopropylpyrazolo-[1,5-a]pyridin-3-yl)-1,4-dihydropyridine-3,5-dicarboxylate.

* * * * *